United States Patent
Schmid et al.

(10) Patent No.: US 7,312,343 B2
(45) Date of Patent: Dec. 25, 2007

(54) SYNTHESIS OF α-AMINO-β-ALKOXY-CARBOXYLIC ACID ESTERS

(75) Inventors: Rudolf Schmid, Basel (CH); Ulrich Zutter, Basel (CH)

(73) Assignee: Hoffmann-La Roche Inc., Nutley, NJ (US)

( * ) Notice: Subject to any disclaimer, the term of this patent is extended or adjusted under 35 U.S.C. 154(b) by 221 days.

(21) Appl. No.: 11/140,319

(22) Filed: May 27, 2005

(65) Prior Publication Data

US 2005/0272665 A1 Dec. 8, 2005

(30) Foreign Application Priority Data

Jun. 2, 2004 (EP) .................. 04102458

(51) Int. Cl.
C07D 207/08 (2006.01)
C07C 211/27 (2006.01)
(52) U.S. Cl. ................ 548/573; 564/384
(58) Field of Classification Search .......... 564/384; 548/573
See application file for complete search history.

(56) References Cited

U.S. PATENT DOCUMENTS

2003/0055002 A1 3/2003 Fujii et al.

FOREIGN PATENT DOCUMENTS

WO WO 03/008378 1/2003

OTHER PUBLICATIONS

Graham, et al., Chem Commun., vol. 11, pp. 966-967 (2001), XP009054987.
Poli, et al., Tetrahedron, vol. 54, pp. 10403-10418 (1998), XP002348955.
Andres, et al., Eur. J. Org. Chem., pp. 1558-1566 (2004), XP002348956.
Andres, et al., Tetrahedron, vol. 57, pp. 8521-8530 (2001), XP002348958.
Gennari, et al., J. Org. Chem., vol. 60, pp. 6248-6249 (1995), XP002348959.
Reetz, et al., Tetrahedon Letters, vol. 33, No. 24, pp. 3453-3456 (1992), XP002348957.
Hanessian, et al., Synlett, pp. 351-352 (1997), XP002348960.
Gennari, et al., Tetrahedron, vol. 53, No. 15, pp. 5593-5608 (1997), XP002348961.
Floersheim, P., et al., Chima, Aarau, CH, vol. 46, No. 7/8, pp. 323-334 (1992), XP000863256.
Hanessian, et al., Angew. Chem. Int. Ed., vol. 40, No. 20, pp. 3810-3813 (2001), XP002348962.
Matsunaga, et al., Heterocycles, vol. 33, No. 1, pp. 235-255 (1992), XP009055491.
Saigo, et al., Chem. Lett. 1976, pp. 769-770.
Mukaiyama, et al., Synthesis 1987, pp. 1043-1054.
Kano, et al., Chem. Lett. 1987, pp. 1531-1534.
Graham, et al., Tetrahedron Lett. 2001, vol. 42, pp. 2865-2868.
Graham, et al., Org. Biomol. Chem. 2003, vol. 1, pp. 834-849.
Pettit, et al., The Dolastatins, Progress in the Chem. Of Organic Natural Compounds, Springer, Vienna, 1997, vol. 70, pp. 1-79.

*Primary Examiner*—Rebecca Anderson
*Assistant Examiner*—Shawquia Young
(74) *Attorney, Agent, or Firm*—George W. Johnston; Patricia S. Rocha-Tramaloni

(57) ABSTRACT

Compounds of formula I

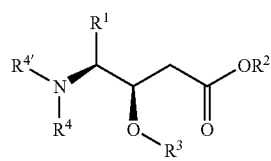

and a process for the preparation of such compounds are disclosed.

5 Claims, No Drawings

SYNTHESIS OF α-AMINO-β-ALKOXY-CARBOXYLIC ACID ESTERS

FIELD OF THE INVENTION

The present invention relates to compounds of formula I

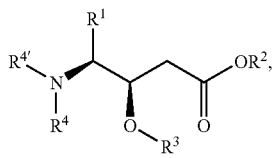

wherein $R^1$-$R^4$ are as herein defined, and to a process (Mukaiyama Aldol reaction) for the preparation of such compounds. Compounds of formula I are useful intermediates in the synthesis of other products, including, e.g. Dolastatin 10.

BACKGROUND OF THE INVENTION

Mukaiyama Aldol reactions are known. Dialkyl acetals are known to be substituted by Mukaiyama aldol reactions with silyl enol ethers or silyl ketene acetals affording β-alkoxy ketones or esters (K. Saigo, M. Osaki, T. Mukaiyama, Chem. Lett. 1976, 769-770; T. Mukaiyama, M. Murakami, Synthesis 1987, 1043-1054; S. Kano, T. Yokomatsu, H. Iwasawa, S. Shibuya, Chem. Lett. 1987, 1531-1534; M. A. Graham, A. H. Wadsworth, M. Thornten-Pett, B.Carrozzini, G. L. Cascarano, C. M. Rayner, Tetrahedron Lett. 2001, 42, 2865-2868; M. A. Graham, A. H. Wadsworth, M. Thornten-Pett, B.Carrozzini, G. L. Cascarano, C. M. Rayner, Org. Biomol. Chem. 2003, 1, 834-849).

Surprisingly, it has now been found that N-benzyl-protected dialkyl acetal derivatives undergo desired aldol reaction with high diastereoselectivity using a Mukaiyama aldol reaction.

SUMMARY OF THE INVENTION

In one embodiment, the present invention relates to a process of the preparation of compounds of formula I

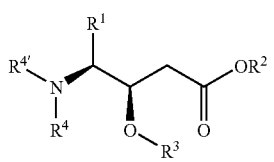

comprising reacting a compound of formula II

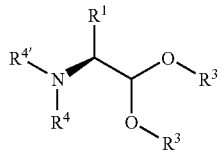

with a compound of formula III

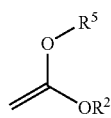

in the presence of a Lewis acid and an organic solvent; wherein $R^1$ is $C_{1-4}$ alkyl, $C_{3-6}$ cycloalkyl-$C_{1-4}$ alkyl or aryl-$C_{1-4}$ alkyl;

$R^2$ is $C_{1-4}$ alkyl, benzyl, substituted benzyl or allyl;

$R^3$ is $C_{1-4}$ alkyl or allyl;

$R^4$ is $C_{1-4}$ alkyl, allyl, benzyl or substituted benzyl;

$R^{4'}$ is benzyl or substituted benzyl; or alternatively $R^1$ and $R^4$ together with the nitrogen to which they are bound form a pyrrolidine group; and $R^5$ is a trialkylsilyl group.

In another embodiment, the invention relates to compounds of formula I as defined above.

In other embodiments, the invention relates to compounds of formula II as described above, and compounds of formula IV and VI as defined below.

DETAILED DESCRIPTION OF THE INVENTION

As used herein, the following terms have the following meanings:

"$C_{1-4}$ alkyl" denotes straight or branched chain hydrocarbon residues containing 1 to 4 carbon atoms, such as methyl, ethyl, n-propyl, isopropyl, n-butyl, sec-butyl, isobutyl or tert-butyl.

Preferably, $C_{1-4}$ alkyl in $R^1$ is methyl, ethyl, n-propyl, isopropyl, n-butyl, sec-butyl (the R or S isomer), isobutyl or tert-butyl. More preferably, $C_{1-4}$ alkyl in $R^1$ is methyl, ethyl, isopropyl or sec-butyl (the R or S isomer). Most preferably it denotes a (S)-sec-butyl group as depicted in Example 1-12.

$C_{1-4}$ alkyl in $R^2$ is preferably methyl, ethyl or tert-butyl, most preferably it denotes a tert-butyl group.

$C_{1-4}$ alkyl in $R^3$ is preferably methyl or ethyl; most preferably it denotes a methyl group.

$C_{1-4}$ alkyl in $R^4$ is preferably methyl or ethyl; most preferably it denotes a methyl group.

The term "$C_{3-6}$ cycloalkyl-$C_{1-4}$ alkyl" as used herein denotes a $C_{3-6}$ cycloalkyl (cyclopropyl, cyclobutyl, cyclopentyl or cyclohexyl) linked to a $C_{1-4}$ alkyl group as defined above. Preferably the term "$C_{3-6}$ cydoalkyl-$C_{1-4}$ alkyl" as used herein denotes a cyclohexylmethyl group.

The term "aryl-$C_{1-4}$ alkyl" as used herein denotes a aryl group as defined below linked to a $C_{1-4}$ alkyl group as defined above. Preferably the term "aryl-$C_{1-4}$ alkyl" as used herein denotes a benzyl group.

The term "aryl" as used herein denotes an optionally substituted phenyl and naphthyl, both optionally benz-fused to an optionally substituted saturated, partially unsaturated or aromatic monocyclic, bicyclic or tricyclic heterocycle or carbocycle e.g. to cyclohexyl or cyclopentyl. Preferably the term "aryl" as used herein denotes a phenyl group.

The term "allyl" means a monovalent radical —$C_3H_5$ which contains a double bond.

The term "benzyl" means the monovalent aryl radical $PhCH_2$—.

The term "substituted benzyl" as used herein for the substituents $R^2$, $R^4$ and $R^{4'}$, denotes the following substituents attached to the benzyl group: 2,4,6-trimethyl, 3-methoxy, 4-methoxy, 2,4-dimethoxy, 3,4-dimethoxy, 3,5-dimethoxy, 2-nitro, 4-nitro, 2,4-dinitro, 4-bromo, 4-phenyl and 3,4-methylene-dioxy.

The term "trialkylsilyl group" as used herein denotes a $Si(C_{1-6}$ alkyl)$_3$, group wherein $C_{1-6}$ alkyl denotes straight or branched chain hydrocarbon residues containing 1 to 6 carbon atoms, such as methyl, ethyl, n-propyl, isopropyl, n-butyl, sec-butyl, isobutyl, tert-butyl, pentyl or hexyl. Preferably the term "trialkylsilyl group" denotes the following groups: dimethyl-tert-butyl-silyl, trimethyl-silyl or triethyl-silyl, most preferably it denotes a dimethyl-tert-butyl-silyl group.

The term "Lewis acid" as used herein denotes to $BF_3$, TMSOTf, $TiCl_4$ or the corresponding solvent complexes, such as $BF_3.OEt_2$ or $BF_3.DMF$, preferably $BF_3.DMF$.

The term "organic solvent" as used for the synthesis of compound of formula I denotes solvents such as dichloromethane MeCN, THF, DMF (N,N-dimethylformamide), $CHCl_3$, toluene or dichlorethane . Most preferably, dichloromethane may be used as the organic solvent.

The term "organic solvent" as used for the synthesis of a compound of formula II (reaction of the compound of formula IV and V) denotes alcohols, such as methanol, ethanol, propanol and butanol. In a preferred embodiment the alcohol depends on the substituent $R^3$. If, for example, $R^3$ is methyl the solvent is methanol.

The term "organic solvent" as used for the synthesis of the compound of formula II (reaction of the compound of formula VI and benzaldehyde) denotes a chlorinated solvent, such as dichloromethane, trichlormethane or dichlorethane. Most preferably, dichloromethane may be used as organic solvent.

The term "acid" as used herein denotes HCl, HBr, $H_2SO_4$, $CF_3SO_3H$ or p-Toluenesulfonic acid. Most preferably the term "acid" denotes $H_2SO_4$ or HCl.

The term "mineral acid" as used herein means HCl, HBr, $H_2SO_4$ or $CF_3SO_3H$, preferably HCl or $H_2SO_4$.

The term "reducing agent" as used herein denotes NaHB(OAc)$_3$ or $NaBH_4$. Most preferably the term "reducing agent" denotes NaHB(OAc)$_3$.

The term "base" as used herein denotes typical N-containing organic bases, such as $Me_3N$, $Et_3N$, or pyridine. Most preferably, the term "base" denotes to $Et_3N$.

In an embodiment of the invention, a compound of formula I

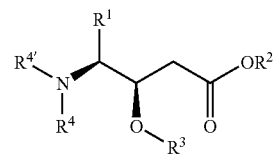

is synthesized by reacting a compound of formula II

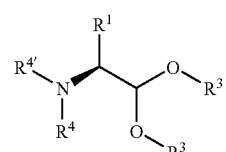

with a compound of formula III

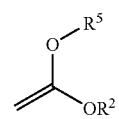

in the presence of a Lewis acid and an organic solvent; wherein $R^1$-$R^5$ are as defined above.

The synthesis of the compound of formula I is carried out at a temperature range of –40° C. to 70° C., preferably at a temperature range of –20° C. to 30° C., and most preferably at a temperature range of –10° C. to 10° C.

In a preferred embodiment of the invention the process for the preparation of the compound of formula II comprises the reaction of a compound of formula IV

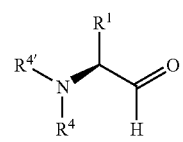

wherein $R^1$ is $C_{1-4}$ alkyl, $C_{3-6}$ cycloalkyl-$C_{1-4}$ alkyl or aryl-$C_{1-4}$ alkyl;

$R^4$ is $C_{1-4}$ alkyl, allyl, benzyl or substituted benzyl;

$R^{4'}$ is benzyl or substituted benzyl, or $R^1$ and $R^4$ together with the nitrogen to which they are bound form a pyrrolidine group;

with a compound of formula V

wherein $R^3$ is $C_{1-4}$ alkyl or allyl;

in the presence of an organic solvent and an acid.

In another embodiment, a compound of formula II may be obtained by contacting a compound of formula VI

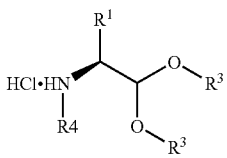

wherein $R^1$ and $R^3$ are as defined above;

with benzaldehyde or substituted benzaldehyde, a reducing agent, a base and an organic solvent.

Preferably, benzaldehyde is used.

The term "substituted benzaldehyde" as used herein for the synthesis of compounds of formula IV (from compounds of formula VI), denotes to the following substituents attached to the phenyl group of the substituted benzaldehyde: 2,4,6-trimethyl, 3-methoxy, 4-methoxy, 2,4-dimethoxy, 3,4-dimethoxy, 3,5-dimethoxy, 2-nitro, 4-nitro, 2,4-dinitro, 4-bromo, 4-phenyl and 3,4-methylene-dioxy.

The substituted benzaldehyde is either commercially available or may be alternatively synthesized according to methods known from textbooks on organic chemistry (e.g. J. March (1992), "Advanced Organic Chemistry: Reactions, Mechanisms, and Structure", $4^{th}$ ed. John Wiley & Sons).

In a further preferred embodiment of the invention the process is carried out wherein $R^1$ is methyl, ethyl, isopropyl or sec-butyl;

$R^2$ is methyl, ethyl or tert-butyl;

$R^3$ is methyl or ethyl;

$R^4$ is $C_{1-4}$ alkyl, allyl or benzyl;

$R^{4'}$ is benzyl;

$R^5$ is dimethyl-tert-butyl-silyl, trimethyl-silyl or triethyl-silyl; and the Lewis acid is $BF_3$, TMSOTf, $TiCl_4$, $BF_3.OEt_2$ or $BF_3.DMF$.

In a further preferred embodiment of the invention the process is carried out wherein $R^1$ is (S)-sec-butyl;

$R^2$ is tert-butyl;

$R^3$ is methyl;

$R^4$ is methyl;

$R^{4'}$ is benzyl;

$R^5$ is dimethyl-tert-butyl-silyl; and the Lewis acid is $BF_3.DMF$.

The compounds of formula I are new and therefore form part of the invention. Preferred are compounds of formula I

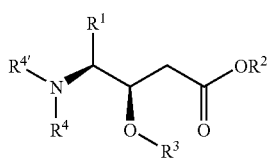

wherein $R^1$ is $C_{1-4}$ alkyl, $C_{3-6}$ cycloalkyl-$C_{1-4}$ alkyl or aryl-$C_{1-4}$ alkyl;

$R^2$ is $C_{1-4}$ alkyl, benzyl, substituted benzyl or allyl;

$R^3$ is $C_{1-4}$ alkyl or allyl;

$R^4$ is $C_{1-4}$ alkyl, allyl, benzyl or substituted benzyl;

$R^{4'}$ is benzyl or substituted benzyl; or alternatively, $R^1$ and $R^4$ together with the nitrogen to which they are bound form a pyrrolidine group.

Also preferred are compounds of formula I wherein $R^1$ is methyl, ethyl, isopropyl, sec-butyl, cyclohexylmethyl, and benzyl $R^2$ is methyl, ethyl or tert-butyl;

$R^3$ is methyl or ethyl;

$R^4$ is methyl, ethyl, allyl or benzyl;

$R^{4'}$ is benzyl.

A further preferred embodiment of the invention is a compound of formula I wherein $R^1$ is (S)-sec-butyl;

$R^2$ is tert-butyl;

$R^3$ is methyl;

$R^4$ is methyl;

$R^{4'}$ is benzyl.

The compounds of formula II are also novel and therefore form part of the invention. Preferred are compounds of formula II

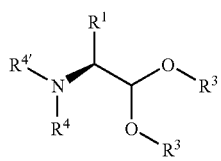

wherein $R^1$ is $C_{1-4}$ alkyl, $C_{3-6}$ cycloalkyl-$C_{1-4}$ alkyl or aryl-$C_{1-4}$ alkyl;

$R^3$ is $C_{1-4}$ alkyl or allyl;

$R^4$ is $C_{1-4}$ alkyl, allyl, benzyl or substituted benzyl;

$R^{4'}$ is benzyl or substituted benzyl; or alternatively, $R^1$ and $R^4$ together with the nitrogen to which they are bound form a pyrrolidine group.

A further preferred embodiment of the invention are compounds of formula II wherein $R^1$ is methyl, ethyl, isopropyl or sec-butyl;

$R^3$ is methyl or ethyl;

$R^4$ is methyl, ethyl, allyl or benzyl; and $R^{4'}$ is benzyl.

A further preferred embodiment of the invention are compounds of formula II wherein $R^1$ is (S)-sec-butyl;

$R^3$ is methyl;

$R^4$ is methyl; and $R^{4'}$ is benzyl.

The compounds of formula IV are new and therefore also form part of the invention. Preferred are compounds of formula IV

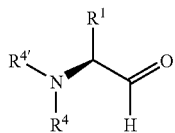

wherein $R^1$ is $C_{1-4}$ alkyl, $C_{3-6}$ cycloalkyl-$C_{1-4}$ alkyl or aryl-$C_{1-4}$ alkyl;

$R^4$ is $C_{1-4}$ alkyl, allyl, benzyl or substituted benzyl;

$R^{4'}$ is benzyl or substituted benzyl, or alternatively, $R^1$ and $R^4$ together with the nitrogen to which they are bound form a pyrrolidine group.

A further preferred embodiment of the invention are compounds of formula IV wherein $R^1$ is methyl, ethyl, isopropyl or sec-butyl;

$R^4$ is methyl, ethyl, allyl or benzyl; and $R^{4'}$ is benzyl.

A further preferred embodiment of the invention are compounds of formula IV wherein $R^1$ is (S)-sec-butyl;

$R^4$ is methyl; and $R^{4'}$ is benzyl.

General synthesis of compounds of formula IV, wherein $R^1$ is $C_{1-4}$ alkyl, $C_{3-6}$ cycloalkyl-$C_{1-4}$ alkyl or aryl-$C_{1-4}$ alkyl;

$R^4$ is $C_{1-4}$ alkyl, allyl, benzyl or substituted benzyl;

$R^{4'}$ is benzyl or substituted benzyl; or alternatively, $R^1$ and $R^4$ together with the nitrogen to which they are bound form a pyrrolidine group, is a follows:

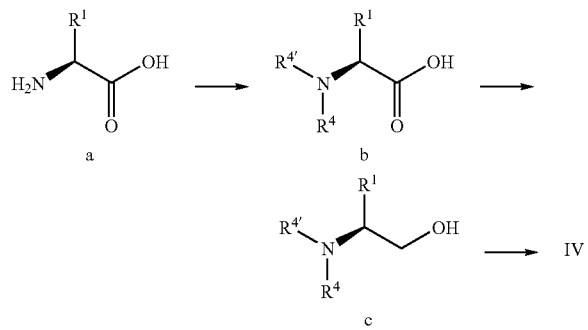

The starting material compound of formula a, wherein $R^1$ is $C_{1-4}$ alkyl, $C_{3-6}$ cycloalkyl-$C_{1-4}$ alkyl or aryl-$C_{1-4}$ alkyl, is either commercially available or can be synthesized according to methods well known to the skilled artisan and as for example disclosed in textbooks on organic chemistry (e.g. J. March (1992), "Advanced Organic Chemistry: Reactions, Mechanisms, and Structure", 4$^{th}$ ed. John Wiley & Sons).

Compounds of formula VI are also new and are an embodiment of the invention.

General synthesis of compounds of formula VI, wherein $R^1$ is $C_{1-4}$ alkyl, $C_{3-6}$ cycloalkyl-$C_{1-4}$ alkyl or aryl-$C_{1-4}$ alkyl; and $R^3$ is $C_{1-4}$ alkyl or allyl; is as follows:

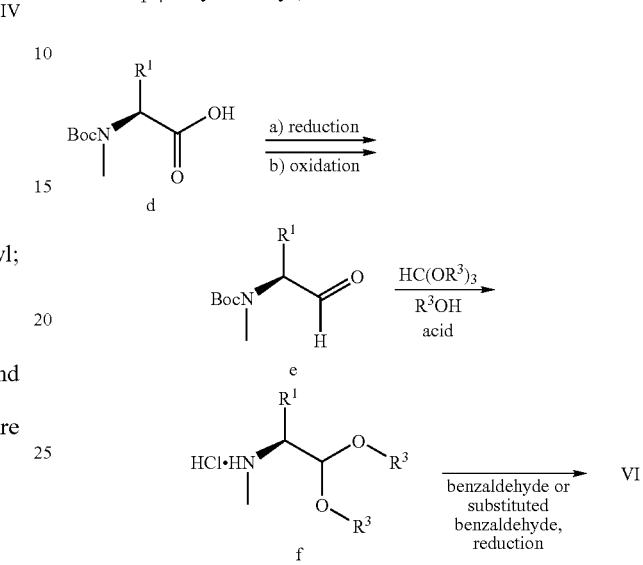

The starting material compound of formula d, wherein $R^1$ is $C_{1-4}$ alkyl, $C_{3-6}$ cycloalkyl-$C_{1-4}$ alkyl or aryl-$C_{1-4}$ alkyl, is either commercially available or can be synthesized according to methods well known to the skilled artisan and as for example described in textbooks on organic chemistry (e.g. J. March (1992), "Advanced Organic Chemistry: Reactions, Mechanisms, and Structure", 4$^{th}$ ed. John Wiley & Sons).

Compound of formula e is reacted with a compound of formula V, wherein $R^3$ is $C_{1-4}$-alkyl or allyl, to obtain a compound of formula f (see also experimental part; example 3).

The compounds of formula I are important building blocks for the production of useful products in the chemical, agricultural and in the pharmaceutical industry. In particular they are useful for the production of anticancer substances as for example *Dolastatin* 10 or derivatives thereof as for example described in G. R. Pettit, "The Dolastatins", Progress in the Chemistry of Organic Natural Compounds, Springer, Vienna 1997, Vol. 70, 1-79, or in WO 03/008378.

Therefore, another embodiment of the present invention is the process as described above, wherein a compound of formula I is further reacted to give a compound of formula A

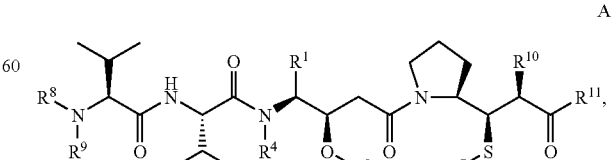

as follows:

a) the benzyl or substituted benzyl group of $R^{4}$ in formula I is cleaved in the presence of hydrochloric acid, hydrogen and a palladium catalyst to give a compound of formula I-A

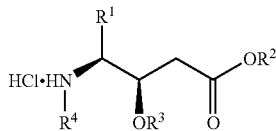

I-A b) said compound of formula I-A is further reacted with an N-protected valine derivative to give, after N-deprotection, a compound of formula B,

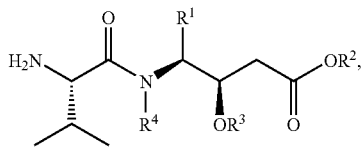

B c) said compound of formula B is further reacted with a compound of formula C

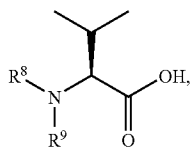

C to give a compound of formula D

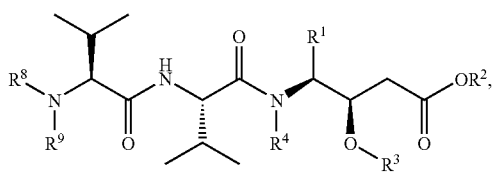

D d) the compound of formula D is further reacted with a compound of formula E

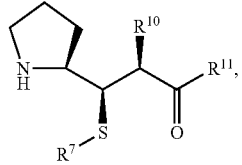

E to give a compound of formula A; wherein $R^1$, $R^2$, $R^3$ and $R^4$ are as defined herein before;

$R^7$, $R^8$, $R^9$ and $R^{10}$ independently from each other represent alkyl; and $R^{11}$ is phenylalkyl-, or phenyldialkylamino or phenylalkyloxy, having ($C_1$-$C_4$)-alkylene and wherein the phenyl group optionally may be substituted with one, two or three substituents selected from the group consisting of halogen, alkoxycarbonyl, sulfamoyl, alkylcarbonyloxy, carbamoyloxy, cyano, mono- or di-alkylamino, alkyl, alkoxy, phenyl, phenoxy, trifluoromethyl, trifluoromethoxy, alkylthio, hydroxy, alkylcarbonylamino, 1,3-dioxolyl, 1,4-dioxolyl, amino and benzyl.

In a preferred embodiment according to the present invention, the N-protected valine derivative in step b) of the process as described above is the compound of formula F,

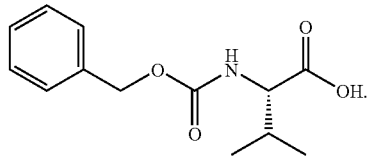

F

Reactions to deprotect N-protected amino acids, as for example valine and/or derivatives thereof as mentioned above are well known to the skilled artisan. According to the present invention, said deprotection of the N-protected valine derivative according to step b) of the process described above is preferably carried out by hydrogenolysis.

Still another embodiment of the present invention is the process as described above, wherein $R^1$ is sec-butyl;

$R^2$ is tert-butyl;

$R^3$, $R^4$, $R^7$, $R^8$, $R^9$, and $R^{10}$ are methyl; and $R^{11}$ is 2-(3-hydroxyphenyl) ethyl-methyl amino.

Still another embodiment of the present invention is the process as described above for the manufacture of the compound of formula A-1

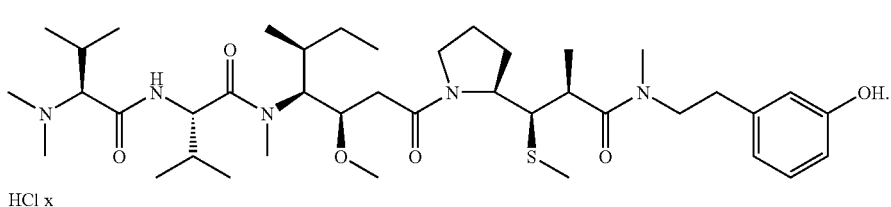

A-1

HCl x

Yet another embodiment of the present invention is the use of the process according to the present invention in the manufacture of the compounds of formula A as defined above.

Yet another embodiment of the present invention is the use of the process according to the present invention in the manufacture of the compound of formula A-1 as defined above.

In the following examples the abbreviations used have the following significations.
NMR nuclear magnetic resonance spectroscopy
IR infra red spectroscopy
HV high vacuum
min minute(s)
h hour(s)
RT room temperature
Me methyl
Et ethyl

EXAMPLE 1

(1S,2S)-(1-Hydroxymethyl-2-methyl-butyl)-methyl-carbamic Acid tert-butyl Ester

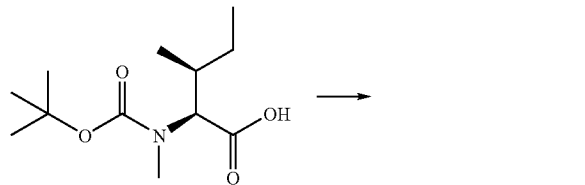

39.3 g Boc-MeIle-OH (0.160 mol; Synthetech) were dissolved in 160 ml THF and cooled to 0° C. 240 ml 1M BH$_3$-THF (0.24 mol; Fluka) were added at 0° C. over 1 h and the clear, colorless reaction mixture was warmed up and stirred at RT for 1 h. The reaction mixture was again cooled to 0° C., 100 ml deionized water were carefully added at 0-5° C. over 0.5 h and after warming up to RT stirring was continued for 1 h. To the colorless solution were added 250 ml 10% Na$_2$CO$_3$ all at once and after stirring for 1 h the reaction mixture was extracted with 1000 ml and 500 ml ethyl acetate. The organic layers were washed with brine and dried (Na$_2$SO$_4$). Removal of the solvent by rotary evaporation gave 36.9 g (99.7%) product as colorless oil.

EXAMPLE 2

(1S,2S)-(1-Formyl-2-methyl-butyl)-methyl-carbamic Acid tert-butyl Ester

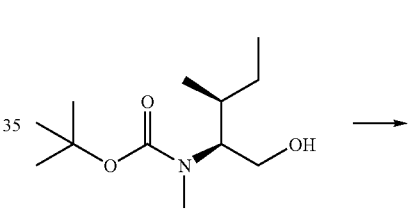

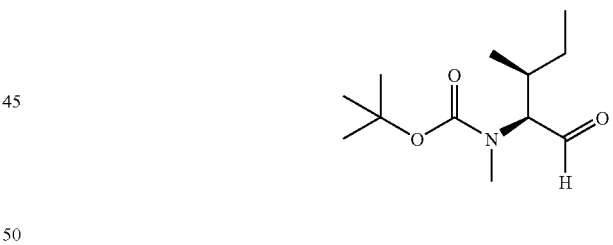

To a solution of 37.0 g Boc-N-methyl-isoleucinol (160 mmol) in 160 ml dichloromethane was added a solution of 5.4 g NaHCO$_3$ (64 mmol) and 1.9 g KBr (16 mmol) in 160 ml deionized water. The reaction mixture was cooled to 0° C. and after the addition of 125 mg 2,2,6,6-tetramethyl-piperidin-1-oxyl (TEMPO, 0.8 mmol), 122.6 g 10.2% aqueous sodium hypochlorite (176 mmol Cl$_2$) were added under stirring over 2.5 h at 0-5°. After additional stirring for 30 min the excess of NaOCl was destroyed by the addition of ca. 1 ml 38% aqueous sodium bisulfite and the reaction mixture was warmed up to 20°. The aqueous layer was extracted with 160 ml dichloromethane and the organic layers were washed with 10% brine and dried (Na$_2$SO$_4$). Removal of the solvent by rotary evaporation afforded 35.7 g (97.2%) crude product as a light orange oil.

EXAMPLE 3

(1S,2S)-(1-Dimethoxymethyl-2-methyl-butyl)-methyl-amine hydrochloride

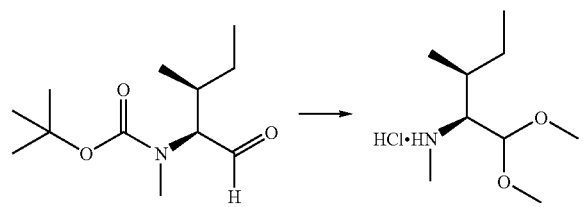

35.6 g Crude aldehyde (160 mmol) were dissolved in 200 ml methanol and cooled to ~15° C. 111 ml 2.8M HCl-MeOH (0.31 mol HCl) were added all at once and the yellowish solution was stirred at RT for 2 h. 155 ml Trimethyl orthoformate (1.42 mol; Fluka) were now added and the reaction mixture was stirred at RT over night (18 h). The solvent and the excess of the orthoester were removed by rotary evaporation (40° C./≧10 mbar) and the resulting beige, crystalline residue (33.7 g) was dissolved in ca. 310 ml isopropyl acetate at ~70° C. After cooling to RT and crystallization at 0° C. for 17 h the crystal suspension was filtered and dried (50° C./10 mbar/16 h) affording 29.6 g product as white needles, mp. 127-128° C. $^1$H-NMR:

EXAMPLE 4

(1S,2S)-Benzyl-(1-dimethoxymethyl-2-methyl-butyl)-methyl-amine

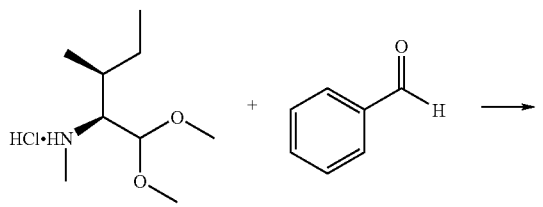

To a solution of 31.76 g the above described hydrochloride (150 mmol) in 600 ml dichloromethane were added 15.94 g triethylamine (157.5 mmol) and 17.51 g benzaldehyde (165 mmol) and the clear light orange solution was stirred at RT for 1 h. 40.16 g sodium triacetoxyborohydride (180 mmol; Aldrich) were added under ice cooling and the white suspension was stirred at RT for 24 h. The reaction mixture was washed with 600 ml 10% $Na_2CO_3$ and twice with 300 ml 10% brine. All three aqueous layers were extracted sequentially with 300 ml dichloromethane and the combined organic layers were dried over $Na_2SO_4$. Filtration and removal of the solvent by rotary evaporation (45° C./≧10 mbar) gave 41.3 g orange oily residue. Purification by vacuum distillation gave 38.4 g (96.5%) product, as colorless oil, b.p. 85-87° C./0.05 mbar. $^1$H-NMR:

EXAMPLE 5

N-Benzyl-L-isoleucine (Bn-Ile-OH)

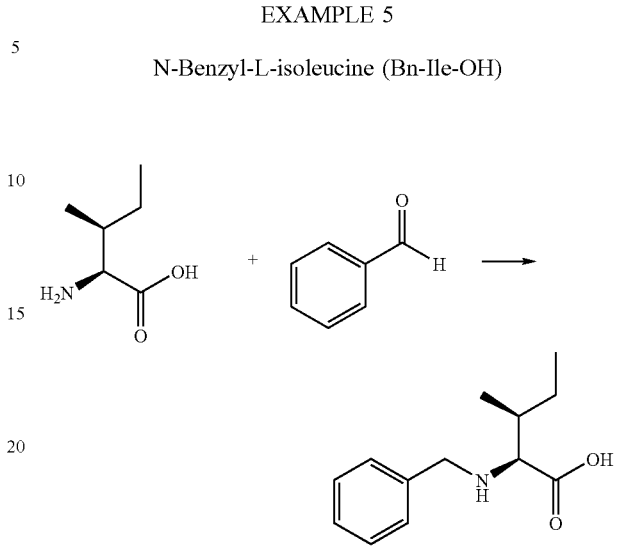

65.6 g L-Isoleucine (500 mmol; Senn Chemicals) were added in portions to 250 ml 2N NaOH (500 mmol) under stirring. After complete dissolution of the amino acid 53.1 g benzaldehyde (500 mmol) were added all at once and stirring was continued at RT for 0.5 h. 5.7 g Sodium borohydride (150 mmol) were now added under stirring in five portions at 5-15° C. and stirring at RT was continued for 3.5 h. The reaction mixture was diluted with 250 ml deionized water and extracted twice with 250 ml diethyl ether. The clear aqueous layer (pH ~14) was now slowly neutralized under vigorous stirring with ca. 400 ml 2N HCl to pH=7 and the white, viscous suspension was stirred at RT for 0.5 h. After filtration and washing with deionized water (2×250 ml), the filter cake was dried (70 h and 70° C./10 mbar/20 h) to yield 103.2 g (93.2%) product as a white powder.

EXAMPLE 6

N-Benzyl-N-methyl-L-isoleucine (Bn-MeIle-OH)

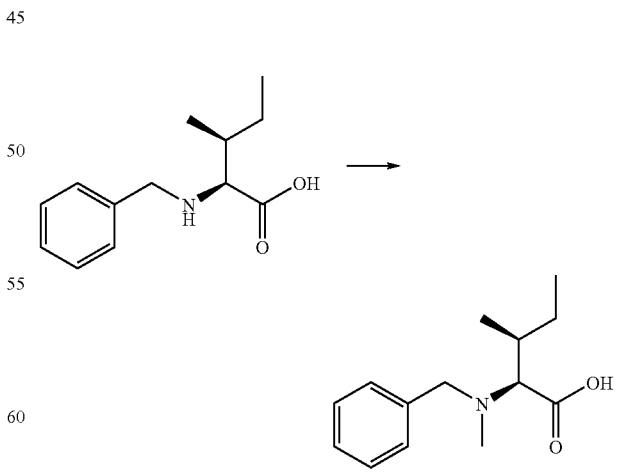

To 110.7 g of above described N-benzyl-isoleucine (0.50 mol) were added 69.0 g formic acid (1.50 mol) and 49.4 g formaldehyde 36.5% in water (0.60 mol) and the clear, colorless reaction mixture was heated under stirring to ~90°

C. for 2 h. The reaction mixture was concentrated by rotary evaporation (60° C./25 mbar) and the residue was triturated under stirring (~15 min) with 250 ml acetone. After evaporation of the solvent, triturating was repeated twice using a total of 500 ml acetone. Evaporation of the solvent (50° C./10 mbar) gave 129.9 g white, crystalline residue which was stirred with 200 ml acetone for 1 h at RT and 3 h at −20° C. The crystal suspension was filtered, washed with cold acetone and dried (16 h/50° C./10 mbar) affording 103.9 g (88.3%) product as a white, crystalline powder.

EXAMPLE 7

N-Benyl-N-methyl-L-isoleucinol

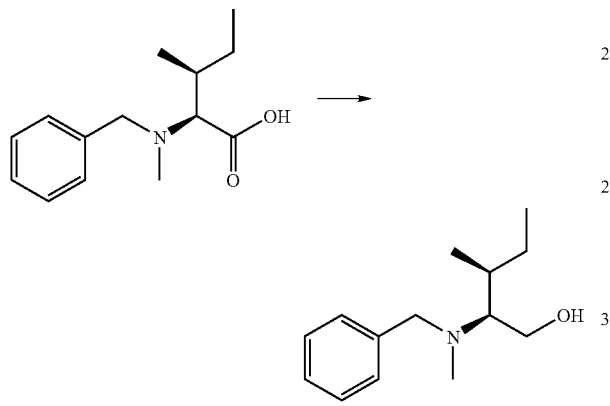

To a grey suspension of 22.8 g lithium aluminum hydride (0.60 mol) in 600 ml tetrahydrofuran were added at 0-10C. 94.1 g N-benzyl-N-methyl-L-isoleucine (0.40 mol) in 6 portions over 20 min. The ice-methanol bath was removed and the reaction mixture was heated up and refluxed for 1.5 h. The reaction mixture was again cooled to 0° C., diluted with 450 ml diethyl ether and then hydrolyzed by the slow addition of 23 ml deionized water. After the addition of 23 ml 15% aqueous NaOH at 0° C. a thick grey suspension was formed. 70 ml Deionized water were added over 0.5 h and the color of the suspension turned from grey to white. Stirring was continued at 0° C. for 15 min and at RT for 0.5 h. The white precipitate was filtered off, washed with 270 ml diethyl ether and the filtrate was evaporated (35° C./≧10 mbar) affording 85.1 g (96.1%) of the product as colorless oil.

EXAMPLE 8

(2S,3S)-2-(Benzyl-methyl-amino)-3-methyl-pentanal

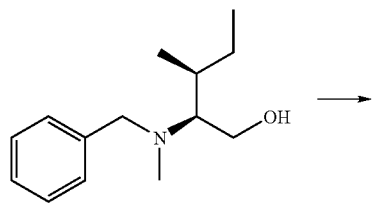

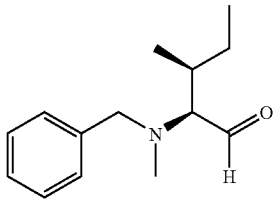

To a stirred solution of 36 ml oxalyl chloride (0.42 mol; Fluka) in 1100 ml dichloromethane were added at −70° C. a solution of 44 ml dimethyl sulfoxide (0.62 mol) in 800 ml dichloromethane over 0.5 h. After stirring at −700 for 15 min a solution of 77.5 g N-benzyl-N-methyl-isoleucinol (0.35 mol) in 700 ml dichloromethane was added at −70° C. over ~0.5 h and stirring was continued for 15 min. After the addition of 234 ml triethylamine (1.68 mol) at −65° C. stirring was continued for 5 min and the white suspension stirred at −50° C. for 1 h. The dry ice-bath was removed and 3000 ml deionized water was added drop wise and under stirring while the reaction mixture was warmed up to RT. The organic layer was washed twice with 2000 ml 10% brine and the organic layer was dried (Na$_2$SO$_4$). Removal of the solvent by rotary evaporation (40° C./≧10 mbar/0.1 mbar, 2 h) yielded 76.9 g (100.2%) yellow oily product which was used without purification in the next step.

EXAMPLE 9

Benzyl-((1S,2S)-1-dimethoxymethyl-2-methyl-butyl)-methyl-amine

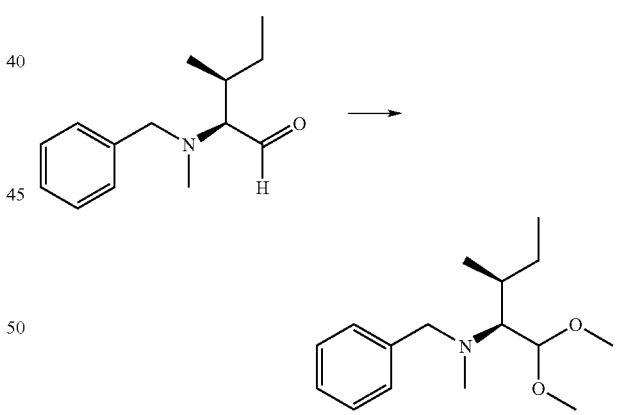

To 76.9 g of the above described aldehyde (0.35 mol) dissolved in 350 ml methanol were added drop wise and under cooling 70 ml conc. H$_2$SO$_4$ (~1.30 mol). After stirring for 0.5 h 350 ml trimethyl orthoformate (3.20 mol; Fluka) were added all at once and stirring at RT was continued for 3 h. The reaction mixture was diluted with 2000 ml ethyl acetate and washed with 2000 ml 10% Na$_2$CO$_3$ and 2000 ml 10% brine. The organic layer was dried (Na$_2$SO$_4$) and evaporated by rotary evaporation (45° C./≧10 mbar) affording 91.9 g yellow oil. Purification by a vacuum distillation gave 86.0 g (92.6%) product as a light yellow oil, b.p. 106° C./0.1 mbar. $^1$H-NMR:

EXAMPLE 10

(1-tert-Butoxy-vinyloxy)-tert-butyl-dimethyl-silane

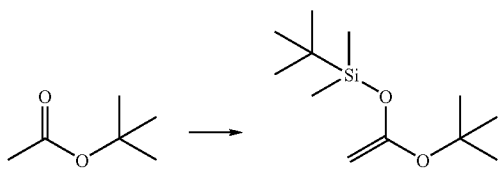

To a stirred solution of 58.2 g diisopropylamine (575 mmol) in 500 ml tetrahydrofuran were added at 0° C. 344 ml 1.6M BuLi in hexane (550 mmol) over 20 min. After stirring for 15 min the solution was cooled to −70° C. and 58.1 g tert-butyl acetate (500 mmol; Fluka) were added at −70° C. over 15 min and stirring continued for 15 min. After the addition of 75 ml HMPA (Fluka) a solution of 81.6 g tert-butyldimethylchlorosilane (525 mmol; Fluka) in 100 ml tetrahydrofuran was added at −70° C. over 15 min and the reaction mixture was warmed to RT over ~1 h. The reaction mixture was concentrated by rotary evaporation (40° C./≧10 mbar) and the honey-oily residue was partitioned between 1000 ml hexane and 1000 ml deionized water. The organic layer was washed with 10% brine (2×500 ml) and dried ($Na_2SO_4$) affording after removal of the solvent by rotary evaporation (40° C./≧10 mbar) 116.1 g bright yellow oil. Purification by vacuum distillation gave 106.0 g (92.0%) product as a colorless oil, b.p. 53-54° C./2.0 mbar. $^1$H-NMR:

EXAMPLE 11

(3R,4S,5S)-4-(Benzyl-methyl-amino)-3-methoxy-5-methyl-heptanoic acid tert-butyl ester (Bn-Dil-OtBu)

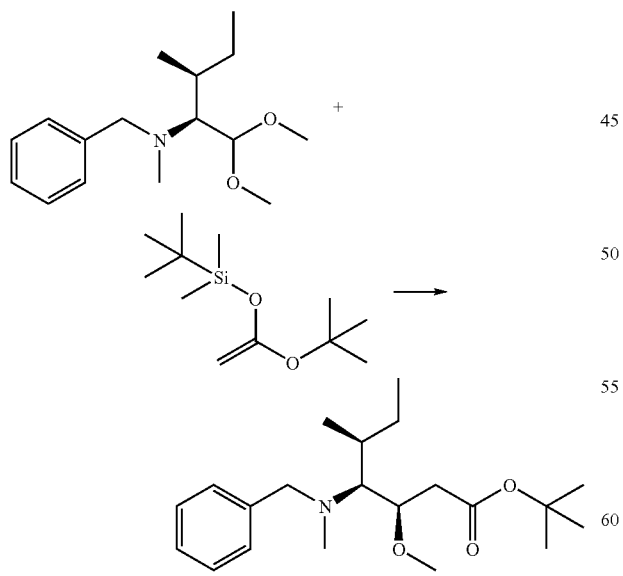

To a stirred solution of the above described 13.27 g dimethylacetal (50 mmol) and the above described 17.28 g TBS-silylketene acetal (75 mmol) in 200 ml dichloromethane was added at 0° C. a solution of 8.04 g N,N-dimethylformamide and 14.19 g boron trifluoride ethyl etherate (100 mmol=12.56 ml; Fluka) in 50 ml dichloromethane over 15 min. After stirring at 0° C. for 24 h the reaction mixture was washed with 250 ml 10% $Na_2CO_3$ and with 10% brine (2×125 ml). The organic layer was ($Na_2SO_4$) and the solvent was removed by rotary evaporation (40° C./≧10 mbar/0.1 mbar, 2 h) yielding 17.5 g (100.1%) crude product as a yellow oil which was used without purification in the next step. OD $[\alpha]_D$=−18.0° ($CHCl_3$; c=1). $^1$H-NMR:

EXAMPLE 12

(3R,4S,5S)-3-Methoxy-5-methyl-4-methylamino-heptanoic acid tert-butyl ester hydrochloride (H-Dil-OtBu.HCl)

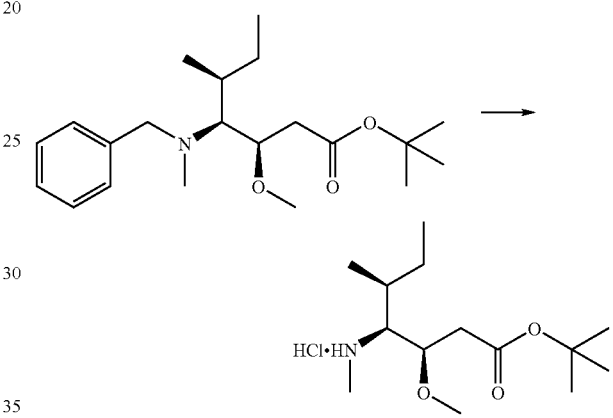

To a stirred solution of 17.5 g of the above described ester (50 mmol) in 250 ml ethanol were added 0.87 g Pd-C 10% (Degussa) and 4.59 ml 37% HCl (55 mmol). The black suspension was hydrogenated under vigorous stirring at RT for 18 h. The flask was flashed with Ar and the black suspension was filtered. After removal of the solvent by rotary evaporation (40° C./≧10 mbar) the white crystalline residue (14.54 g) was dissolved in 350 ml ethyl acetate at ~80° C. After cooling to RT and crystallization under stirring at 0° C. for 17 h the crystal suspension was filtered, washed with −20° cold ethyl acetate and dried (50° C./10 mbar/16 h) affording 12.87 g (87.0% over two steps) white crystalline product, m.p. 153-154° C. (dec.). OD $[\alpha]_D$=+6.71° ($CHCl_3$; c=1). MS ($[M+1]^+$ of the free base). $^1$H-NMR:

EXAMPLE 13

((S)-1-Hydroxymethyl-2-methyl-propyl)-methyl-carbamic acid tert-butyl ester

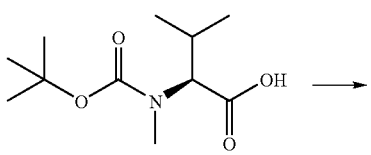

-continued

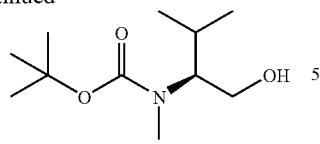

20.0 g Boc-MeVal-OH (86.5 mmol; Fluka) were dissolved in 80 ml THF and cooled to 0° C. 130 ml 1M BH₃-THF (0.13 mol; Fluka) were added at 0° C. over 1 h and the clear, colo reaction mixture was warmed up and stirred at RT for 1 h. The reaction mixture was again cooled to 0° C., 75 ml deionized water were carefully added at 0-5° C. over 0.5 h and after warming up to RT stirring was continued for 1 h. To the colorless solution were added 150 ml 10% Na₂CO₃ all at once and after stirring for 1 h the reaction mixture was extracted with 600 ml and 300 ml ethyl acetate. The organic layers were washed with brine and dried (Na₂SO₄). Removal of the solvent by rotary evaporation gave 17.4 g (94%) product as colorless oil. ¹H-NMR:

EXAMPLE 14

((S)-1-Formyl-2-methyl-propyl)-methyl-carbamic acid tert-butyl ester

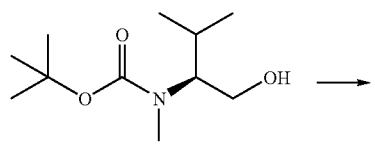

To a solution of 10.5 g Boc-N-methyl-valinol (48.3 mmol) in 50 ml dichloromethane was added a solution of 1.63 g NaHCO₃ (19.3 mmol) and 0.58 g KBr (4.8 mmol) in 50 ml deionized water. The reaction mixture was cooled to 0° C. and after the addition of 77 mg 2,2,6,6-tetramethyl-piperidin-1-oxyl (TEMPO, 0.48 mmol), 36.6 g 10.3% aqueous sodium hypochlorite (53.1 mmol Cl₂) were added under stirring over 2.5 h at 0-5°. After additional stirring for 30 min the excess of NaOCl was destroyed by the addition 38% aqueous sodium bisulfite and the reaction mixture was warmed up to 20°. The aqueous layer was extracted with 50 ml dichloromethane and the organic layers were washed with 50 ml 10% brine and dried (Na₂SO₄). Removal of the solvent by rotary evaporation afforded 9.9 g (95%) crude product as a light orange oil, $[\alpha]_D=-130$ (CHCl₃; c=1). ¹H-NMR:

EXAMPLE 15

((S)-1-Dimethoxymethyl-2-methyl-propyl)-methyl-amine hydrochloride

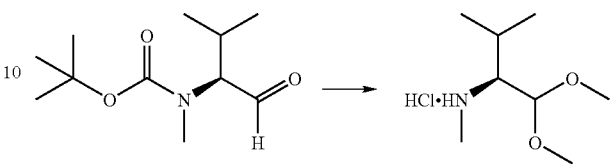

5.0 g Crude Boc-N-methyl-valinal (23.2 mmol) were dissolved in 40 ml methanol and cooled to ~15° C. A solution of 3.3 ml (46.4 mmol) acetyl chloride in 10 ml methanol was added all at once and the yellowish solution was stirred at RT for 1 h (gas evolution). 22.2 g Trimethyl orthoformate (209 mmol) were now added and the reaction mixture was stirred at RT over night (18 h). The solvent and the excess of the orthoester were removed by rotary evaporation (40° C./≧10 mbar) and the resulting beige, crystalline residue (4.6 g) was dissolved in ca. 45 ml isopropyl acetate at ~70° C. After cooling to RT and crystallization at –20° C. for 17 h the crystal suspension was filtered and dried (50° C./10 mbar/16 h) affording 3.2 g (69%) product as greenish needles, $[\alpha]_D=40.3$ (CHCl₃; c=1). ¹H-NMR:

EXAMPLE 16

Benzyl-((S)-1-dimethoxymethyl-2-methyl-propyl)-methyl-amine

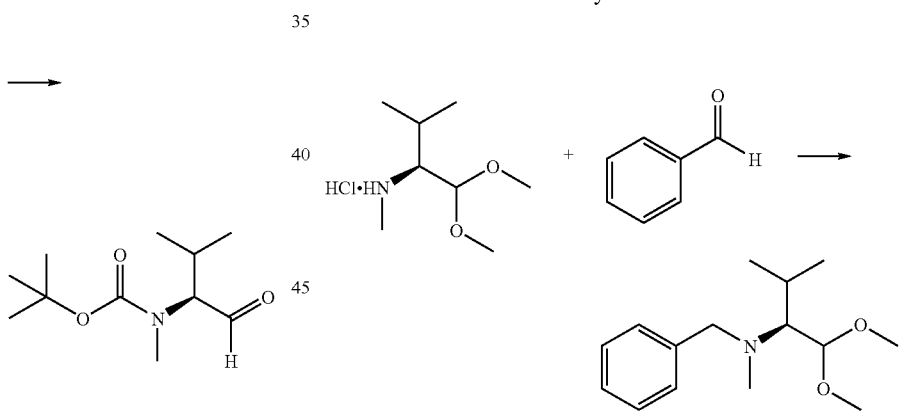

To a solution of 7.13 g the above N-Me-Valinal dimethylacetal hydrochloride (36.1 mmol) in 140 ml dichloromethane were added 3.83 g triethylamine (37.9 mmol) and 4.21 g benzaldehyde (39.7 mmol) and the solution was stirred at RT for 0.5 h. 10.2 g sodium triacetoxyborohydride (43.3 mmol; Aldrich) were added under ice cooling and the white suspension was stirred at RT for 22 h. The reaction mixture was washed with 100 ml 10% Na₂CO₃ and twice with 100 ml 10% brine. All three aqueous layers were extracted sequentially with 200 ml dichloromethane and the combined organic layers were dried over Na₂SO₄. Filtration and removal of the solvent by rotary evaporation (45° C./≧10 mbar) gave 9.54 g orange oily residue. Purification by vacuum distillation gave 8.34 g (92%) product, as light yellow oil, b.p. 86° C./0.2 mbar, $[\alpha]_D=-21.8$ (CHCl₃; c=1). ¹H-NMR:

EXAMPLE 17

(3R,4S)-4-(Benzyl-methyl-amino)-3-methoxy-5-methyl-hexanoic acid tert-butyl ester

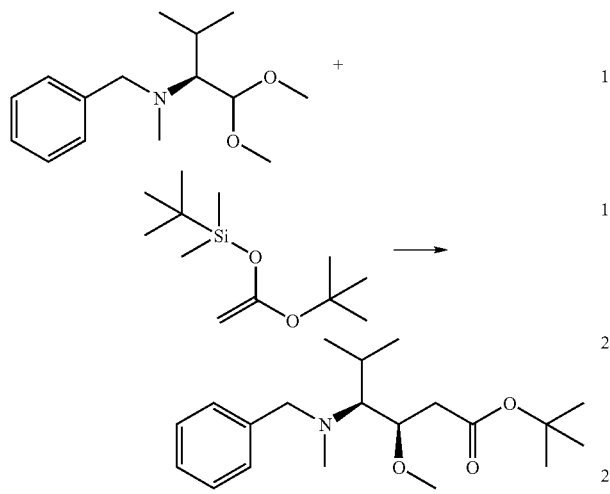

To a stirred solution of the above described dimethylacetal 7.54 g (30 mmol) and the above described TBS-silylketene acetal 10.4 g (45 mmol) in 110 ml dichloromethane was added at 0° C. a solution of 4.83 g (66 mmol) N,N-dimethylformamide and 8.52 g boron trifluoride ethyl etherate (60 mmol=12.56 ml; Fluka) in 30 ml dichloromethane over 15 min. After stirring at 0° C. for 69 h the reaction mixture was washed with 150 ml 10% Na$_2$CO$_3$ and with 10% brine (2×80 ml). The organic layer was dried (Na$_2$SO$_4$) and the solvent was removed by rotary evaporation (40° C./≧20 mbar/0.1 mbar, 2 h) yielding 10.1 g (100%) crude product as a yellow oil which was used without purification in the next step, [α]$_D$=−20.2 (CHCl$_3$; c=1). $^1$H-NMR:

EXAMPLE 18

(3R,4S)-3-Methoxy-5-methyl-4-methylamino-hexanoic acid tert-butyl ester hydrochloride

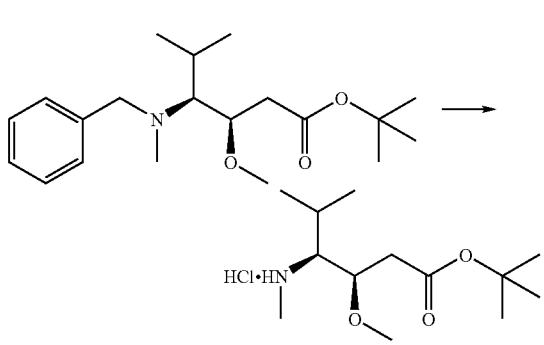

To a stirred solution of 10.0 g of the above described ester (30 mmol) in 150 ml ethanol were added 1.0 g Pd-C 10% (Degussa) and 2.6 ml 37% HCl (31.2 mmol). The black suspension was hydrogenated under vigorous stirring at RT for 18 h. The flask was flashed with Ar and the black suspension was filtered. After removal of the solvent by rotary evaporation (40° C./≧10 mbar) the white crystalline residue (8.76 g) was dissolved in 25 ml hot isopropyl acetate at ~80° C. After cooling to RT and crystallization under stirring at −15° C. for 17 h the crystal suspension was filtered, washed with −20° cold isopropyl acetate and dried (50° C./10 mbar/16 h) affording 4.84 g (57.0% over two steps) white crystalline product, [α]$_D$32 7.9 (CHCl$_3$; c=1). $^1$H-NMR:

EXAMPLE 19

((S)-2-Hydroxy-1-methyl-ethyl)-methyl-carbamic acid tert-butyl ester

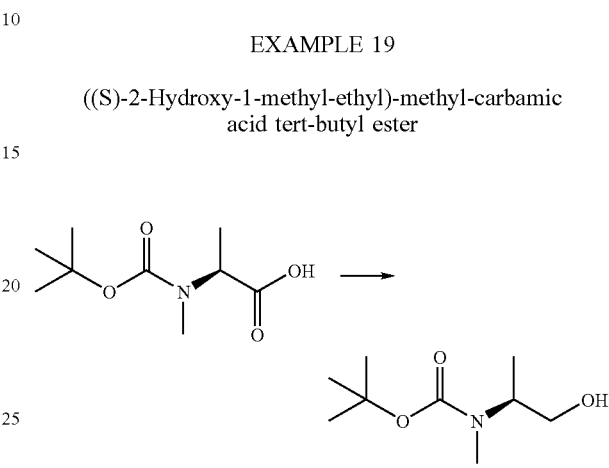

20.3 g Boc-MeAla-OH (100 mmol; Fluka) were dissolved in 80 ml THF and cooled to 0° C. 150 ml 1M BH$_3$-THF (150 mmol; Fluka) were added at 0° C. over 1 h and after additional stirring at 0° C. for 1 h, 65 ml deionized water were added carefully at 0-5° C. After warming up to RT 160 ml 10% Na$_2$CO$_3$ were added and stirring continued for 1 h. The reaction mixture was extracted with 500 ml and 400 ml ethyl acetate and the organic layers were washed with brine and dried (Na$_2$SO$_4$). Removal of the solvent by rotary evaporation gave 18.5 g (98%) product as a colorless oil, [α]$_D$=−6.1 (CHCl$_3$; c=1). $^1$H-NMR:

EXAMPLE 20

Methyl-((S)-1-methyl-2-oxo-ethyl)-carbamic acid tert-butyl ester

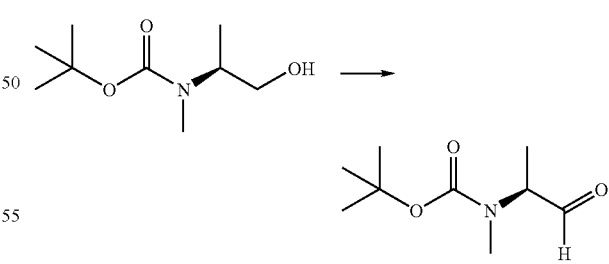

To a solution of 18.0 g Boc-N-methyl-alaninol (95 mmol) in 95 ml dichloromethane was added a solution of 3.2 g NaHCO$_3$ (38 mmol) and 1.14 g KBr (9.5 mmol) in 95 ml deionized water. The reaction mixture was cooled to 0° C. and after the addition of 152 mg 2,2,6,6-tetramethyl-piperidin-1-oxyl (TEMPO, 0.95 mmol), 72 g 10.3% aqueous sodium hypochlorite (105 mmol Cl$_2$) were added under stirring over 2.5 h at 0-5°. After additional stirring for 30 min the excess of NaOCl was destroyed by the addition 38% aqueous sodium bisulfite (1 ml) and the reaction mixture was warmed up to 20°. The aqueous layer was extracted with 100 ml dichloromethane and the organic layers were washed with 100 ml 10% brine and dried (Na$_2$SO$_4$). Removal of the solvent by rotary evaporation afforded 14.4 g (80%) crude product as a light orange oil, $[\alpha]_D$=−82 (CHCl$_3$; c=1). $^1$H-NMR:

EXAMPLE 21

((S)-2,2-Dimethoxy-1-methyl-ethyl)-methyl-amine hydrochloride

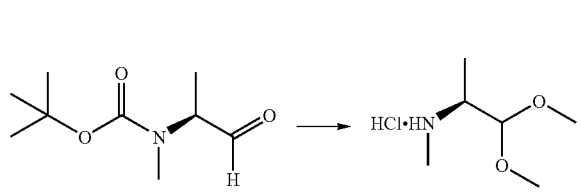

13.1 g Crude Boc-N-methyl-alaninal (70 mmol) were dissolved in 100 ml methanol and cooled to ~15° C. A solution of 11 g (140 mmol) acetyl chloride in 30 ml methanol was added all at once and the yellowish solution was stirred at RT for 1 h (gas evolution). 67.52 g Trimethyl orthoformate (630 mmol) were now added and the reaction mixture was stirred at RT over night (18 h). The solvent and the excess of the orthoester were removed by rotary evaporation (40° C./≧10 mbar) and the resulting 11.9 (100%) beige, crystalline residue was crystallized from 120 ml hot isopropyl acetate yielding after stirring at −20° C. for 17 h 8.4 g (71%) beige product, $[\alpha]_D$=10.8 (CHCl$_3$; c=1). $^1$H-NMR:

EXAMPLE 22

Benzyl-((S)-2,2-dimethoxy-1-methyl-ethyl)-methyl-amine

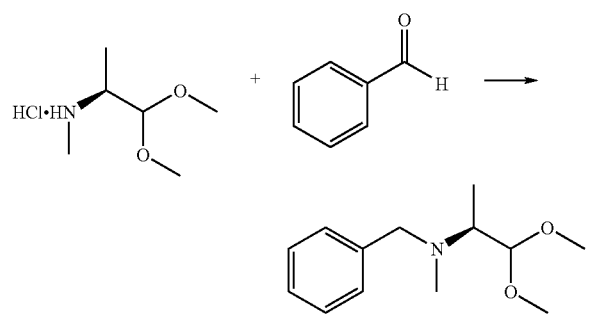

To a solution of 7.63 g the above N-Methyl-alaninal dimethylacetal hydrochloride (45 mmol) in 180 ml dichloromethane were added 4.78 g triethylamine (47.2 mmol) and 5.25 g benzaldehyde (49.5 mmol) and the solution was stirred at RT for 0.5 h. 12.7 g sodium triacetoxyborohydride (54 mmol; Aldrich) were added under ice cooling and the white suspension was stirred at RT for 22 h. The reaction mixture was washed with 180 ml 10% Na$_2$CO$_3$ and twice with 90 ml 10% brine. All three aqueous layers were extracted sequentially with 100 ml dichloromethane and the combined organic layers were dried over Na$_2$SO$_4$ Filtration and removal of the solvent by rotary evaporation (45° C./≧10 mbar) gave 10.0 g orange oily residue. Purification by vacuum distillation gave 8.1 g (80%) product, as light yellow oil, b.p. 119° C./0.8 mbar, $[\alpha]_D$=−2.2 (CHCl$_3$;$_{c=}$1). $^1$H-NMR:

EXAMPLE 23

(3R,4S)-4-(Benzyl-methyl-amino)-3-methoxy-pentanoic acid tert-butyl ester

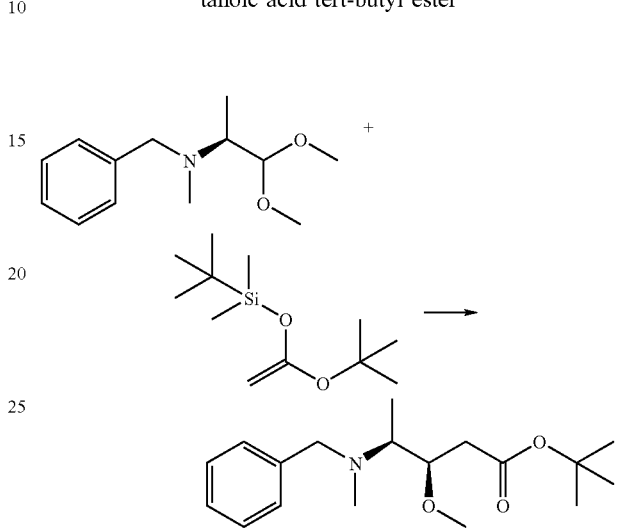

To a stirred solution of the above described 2.90 g dimethylacetal (13 mmol) and the above described 8.99 g TBS-silylketene acetal (39 mmol) in 50 ml dichloromethane was added at 0° C. a solution of 5.70 g N,N-dimethylformamide (78 mmol) and 5.53 g boron trifluoride ethyl etherate (39 mmol=12.56 ml; Fluka) in 13 ml dichloromethane. After stirring at 0° C. for 24 h the reaction mixture was washed with 65 ml 10% Na$_2$CO$_3$ and with 10% brine (2×30 ml). The organic layer was dried (Na$_2$SO$_4$) and the solvent was removed by rotary evaporation (40° C./≧10 mbar/0.1 mbar, 2 h) yielding 4.66 g crude product as a yellow oil which was chromatographed over silica (200 g) with toluene-ethyl acetate 19:1 (30 ml fractions). Evaporation of fraction 21-40 gave 2.97 g (74%) yellow oil. $^1$H-NMR:

EXAMPLE 24

(3R,4S)-3-Methoxy-4-methylamino-pentanoic acid tert-butyl ester hydrochloride

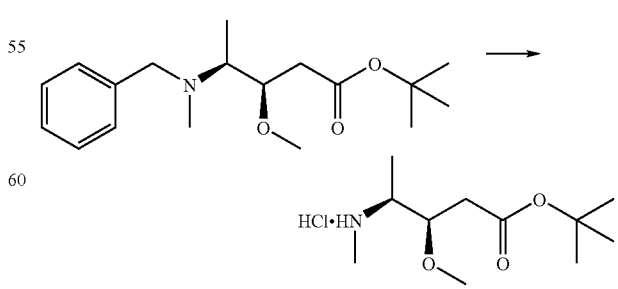

To a stirred solution of 1.54 g of the above described ester (5 mmol) in 25 ml ethanol were added 0.15 g Pd-C 10%

(Degussa) and 0.52 g 37% HCl (5.2 mmol). The black suspension was hydrogenated under vigorous stirring at RT for 2 h. The flask was flashed with Ar and the black suspension was filtered. After removal of the solvent by rotary evaporation (40° C./≧10 mbar) the white crystalline residue (1.19 g) was dissolved in hot acetonitrile (8 ml) and crystallized at 0° C. yielding 1.02 g (80%) beige product, [α]$_D$=6.2 (CHCl$_3$; c=1) $^1$H-NMR:

EXAMPLE 25

(S)-2-Dimethoxymethyl-pyrrolidine hydrochloride

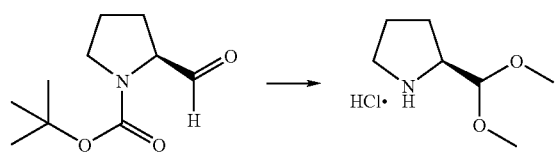

13.9 g Crude Boc-prolinal (70 mmol; Omega Chem, freshly distilled) were dissolved in 110 ml methanol and cooled to ~15° C. A solution of 11.0 g (140 mmol) acetyl chloride in 30 ml methanol was added all at once and the yellowish solution was stirred at RT for 1 h (gas evolution). 66.9 g Trimethyl orthoformate (630 mmol) were now added and the reaction mixture was stirred at RT for 42 h. The solvent and the excess of the orthoester were removed by rotary evaporation (40° C./≧10 mbar) and the resulting 14.0 g beige, crystalline residue was crystallized from 300 ml hot ethyl acetate yielding after stirring at 0° C. for 17 h 8.9 g (70%) white needles, [α]$_D$=−15.4 (CHCl$_3$; c=1). $^1$H-NMR:

EXAMPLE 26

(S)-1-Benzyl-2-dimethoxymethyl-pyrrolidine

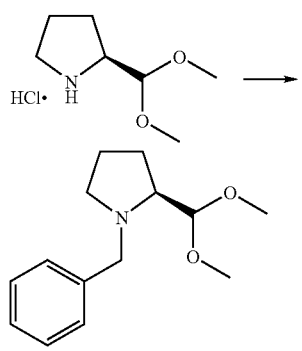

To a solution of 8.2 g of the above described prolinal dimethylacetal hydrochloride (45 mmol) in 150 ml dichloromethane were added 4.78 g triethylamine (47.2 mmol) and 5.25 g benzaldehyde (49.5 mmol) and the solution was stirred at RT for 0.5 h. 12.7 g sodium triacetoxyborohydride (54 mmol; Aldrich) were added under ice cooling and the white suspension was stirred at RT for 26 h. The reaction mixture was washed with 180 ml 10% Na$_2$CO$_3$ and twice with 90 ml 10% brine. All three aqueous layers were extracted sequentially with 90 ml dichloromethane and the combined organic layers were dried over Na$_2$SO$_4$. Filtration and removal of the solvent by rotary evaporation (45° C./≧10 mbar) gave 10.5 g yellow oily residue. Purification by vacuum distillation gave 8.93 g (84%) product, as a colorless oil, b.p. 120° C./0.4 mbar, [α]$_D$=−73.8 (CHCl$_3$; c=1). $^1$H-NMR:

EXAMPLE 27

(R)-3-((S)-1-Benzyl-pyrrolidin-2-yl)-3-methoxy-propionic acid tert-butyl ester

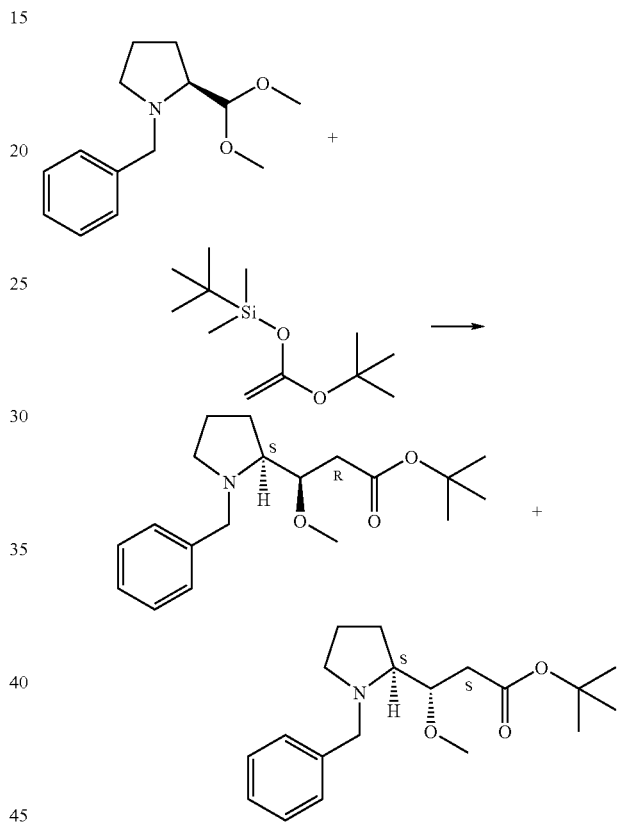

To a stirred solution of the above described dimethylacetal 4.71 g (20 mmol) and the above described TBS-silylketene acetal 13.83 g (60 mmol) in 75 ml dichloromethane was added at 0° C. a solution of 6.43 g (88 mmol) N,N-dimethylformamide and 11.35 g boron trifluoride ethyl etherate (80 mmol) in 25 ml dichloromethane. After stirring at 0° C. for 24 h the reaction mixture was washed with 100 ml 10% Na$_2$CO$_3$ and with 10% brine (50 ml). The organic layer was dried (Na$_2$SO$_4$) and the solvent was removed by rotary evaporation (40° C./≧10 mbar/0.1 mbar, 2 h) yielding 10.2 g crude oily product as a ca. 2:1 mixture of two diastereoisomers. Chromatography over silica (700 g) with hexane-ethyl acetate 14:1 (200 ml fractions) gave 2.49 g oily (3R,4S)-diastereomer (39%; fractions 14-30) and 1.23 g (3S,4S)-diastereomer (19%; fractions 35-44). (3R,4S)-diastereomer: [α]$_D$=−88.7 (CHCl$_3$; c=1) (3R,4S)-diastereomer: $^1$H-NMR:

(3S,4S)-diastereomer: 1H-NMR:

EXAMPLE 28

(R)-3-Methoxy-3-(S)-pyrrolidin-2-yl-propionic acid tert-butyl ester hydrochloride

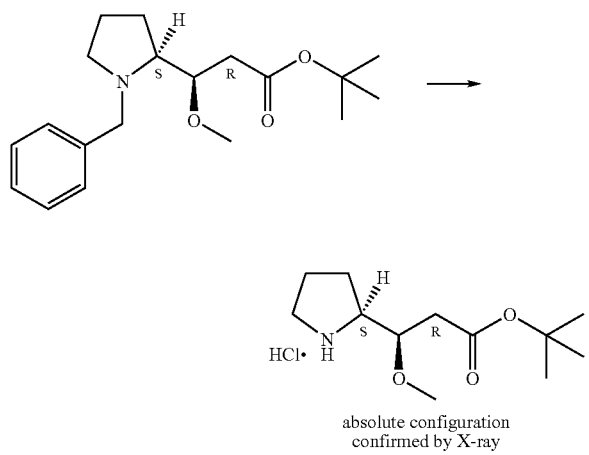

absolute configuration confirmed by X-ray

To a stirred solution of 1.92 g of the above described ester (6 mmol) in 30 ml ethanol were added 0.20 g Pd-C 10% (Degussa) and 0.62 g 37% HCl (6.3 mmol). The black suspension was hydrogenated under vigorous stirring at RT for 2 h. The flask was flashed with Ar and the black suspension was filtered. After removal of the solvent by rotary evaporation (40° C./≧10 mbar) the white crystalline residue (1.57 g) was dissolved in 7.5 ml hot isopropyl acetate at ~80° C. Crystallization at −20° C. yielding 1.37 g (86%) white crystalline product, $[\alpha]_D$=−36.4 (CHCl$_3$; c=1). $^1$H-NMR:

What is claimed is:

1. A process for the preparation of a compound of formula I

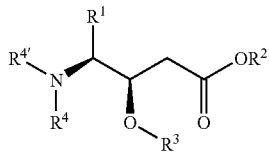

comprising reacting a compound of formula II

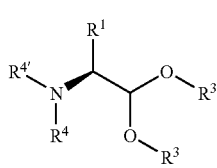

with a compound of formula III

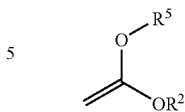

in the presence of a Lewis acid and an organic solvent; wherein $R^1$ is $C_{1-4}$ alkyl, $C_{3-6}$ cycloalkyl-$C_{1-4}$ alkyl or aryl-$C_{1-4}$ alkyl;
$R^2$ is $C_{1-4}$ alkyl, benzyl, substituted benzyl or allyl;
$R^3$ is $C_{1-4}$ alkyl or allyl;
$R^4$ is $C_{1-4}$ alkyl, allyl, benzyl or substituted benzyl;
$R^{4'}$ is benzyl or substituted benzyl; or alternatively,
$R^1$ and $R^4$ together with the nitrogen to which they are bound form a pyrrolidine group; and
$R^5$ is a trialkylsilyl group.

2. The process according to claim 1, wherein
$R^1$ is methyl, ethyl, isopropyl or sec-butyl;
$R^2$ is methyl, ethyl or tert-butyl;
$R^3$ is methyl or ethyl;
$R^4$ is $C_{1-4}$ alkyl, allyl or benzyl;
$R^{4'}$ is benzyl;
$R^5$ is dimethyl-tert-butyl-silyl, trimethyl-silyl or triethyl-silyl; and
the Lewis acid is BF$_3$, TMSOTf, TiCl$_4$, BF$_3$.OEt$_2$ or BF$_3$.DMF.

3. The process according to claim 1, wherein
$R^1$ is (S)-sec-butyl;
$R^2$ is tert-butyl;
$R^3$ and $R^4$ are methyl;
$R^{4'}$ is benzyl;
$R^5$ is dimethyl-tert-butyl-silyl; and
the Lewis acid is BF$_3$.DMF.

4. A compound of formula I

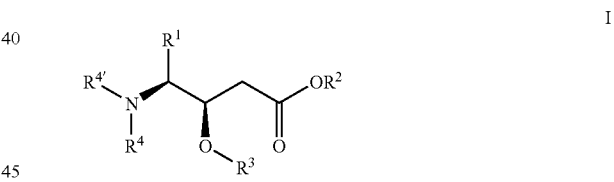

wherein
$R^1$ is $C_{1-4}$ alkyl, $C_{3-6}$ cycloalkyl-$C_{1-4}$ alkyl or aryl-$C_{1-4}$ alkyl;
$R^2$ is $C_{1-4}$ alkyl, benzyl, substituted benzyl or allyl;
$R^3$ is $C_{1-4}$ alkyl or allyl;
$R^4$ is $C_{1-4}$ alkyl, allyl, benzyl or substituted benzyl; and
$R^{4'}$ benzyl or substituted benzyl; or alternatively,
$R^1$ and $R^4$ together with the nitrogen to which they are bound form a pyrrolidine group;
and wherein "substituted benzyl" denotes a benzyl group substituted with a group selected from 2,4,6-trimethyl, 3-methoxy, 4-methoxy, 2,4-dimethoxy, 3,4-dimethoxy, 3,5-dimethoxy, 2-nitro, 4-nitro, 2,4-dinitro, 4-bromo, 4-phenyl or 3,4-methylene-dioxy.

5. The compound according to claim 4, wherein
$R^1$ is methyl, ethyl, isopropyl or sec-butyl;
$R^2$ is methyl, ethyl or tert-butyl;
$R^3$ methyl or ethyl;
$R^4$ is $C_{1-4}$ alkyl, allyl or benzyl; and
$R^4$ is benzyl.

* * * * *